US008504160B2

(12) United States Patent  
Lee et al.

(10) Patent No.: US 8,504,160 B2
(45) Date of Patent: Aug. 6, 2013

(54) SYSTEM AND METHOD FOR MODULATING ACTION POTENTIAL PROPAGATION DURING SPINAL CORD STIMULATION

(75) Inventors: Dongchul Lee, Valencia, CA (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 655 days.

(21) Appl. No.: 12/618,563

(22) Filed: Nov. 13, 2009

(65) Prior Publication Data

US 2010/0125313 A1    May 20, 2010

Related U.S. Application Data

(60) Provisional application No. 61/114,965, filed on Nov. 14, 2008.

(51) Int. Cl.
*A61N 1/00* (2006.01)

(52) U.S. Cl.
USPC .............................................. 607/46; 607/66

(58) Field of Classification Search
USPC ......................................... 607/45–46, 66–72
See application file for complete search history.

(56) References Cited

U.S. PATENT DOCUMENTS

| | | | |
|---|---|---|---|
| 5,501,703 A | 3/1996 | Holsheimer et al. | |
| 6,516,227 B1 | 2/2003 | Meadows et al. | |
| 6,895,280 B2 | 5/2005 | Meadows et al. | |
| 6,928,320 B2 | 8/2005 | King | |
| 6,993,384 B2 | 1/2006 | Bradley et al. | |
| 7,203,548 B2 | 4/2007 | Whitehurst et al. | |
| 7,539,538 B2 | 5/2009 | Parramon et al. | |
| 2003/0139781 A1 | 7/2003 | Bradley et al. | |
| 2005/0267546 A1 | 12/2005 | Parramon et al. | |
| 2005/0278001 A1* | 12/2005 | Qin et al. | 607/48 |
| 2006/0173510 A1* | 8/2006 | Besio et al. | 607/45 |
| 2008/0294226 A1 | 11/2008 | Moffitt et al. | |
| 2009/0024189 A1* | 1/2009 | Lee et al. | 607/66 |
| 2010/0106231 A1* | 4/2010 | Torgerson et al. | 607/116 |
| 2011/0307029 A1* | 12/2011 | Hargrove | 607/45 |

OTHER PUBLICATIONS

U.S. Appl. No. 60/951,177, Use of Stimulation Pulse Shape to Control Neural Recruitment Order and Clinical Effect, filed Jul. 20, 2007.

(Continued)

*Primary Examiner* — Christopher D Koharski
*Assistant Examiner* — Catherine Voorhees
(74) *Attorney, Agent, or Firm* — Vista IP Law Group LLP

(57) ABSTRACT

A method and neurostimulator for providing therapy to a patient is provided. In one technique, an electrical pulsed waveform is conveyed between a caudal electrode and spinal cord tissue, thereby evoking action potentials that are orthodromically propagated along dorsal column fibers and evoking action potentials that are antidromically propagated along the DC fibers. Electrical energy is conveyed between a rostral electrode and the spinal cord tissue, thereby modulating times that the action potentials orthodromically propagated along the DC fibers arrive at the brain. In another technique, an electrical pulsed waveform is conveyed through a first electrode, thereby evoking action potentials that are propagated along a neural axon, and electrical energy is conveyed through the second electrode. The electrical energy has a frequency that is greater than a pulse rate of the electrical pulsed waveform, such that the action potentials propagated along the neural axon are blocked by the electrical energy.

29 Claims, 8 Drawing Sheets

OTHER PUBLICATIONS

Kilgore, K.L. et al., Nerve conduction block utilising high-frequency alternating current, Med. Biol. Eng. Comput. (2004) 42, 394-406.

Bhadra, Niloy, MD. PhD. et al., High-Frequency Electrical Conduction Block of Mammalian Peripheral Motor Nerve, Muscle Nerve (2005) 32: 782-790.

Bhadra, Narendra et al., High frequency electrical conduction block of the pudendal nerve, J. Neural Eng. 3 (2006) 180-187.

Bhadra, Niloy et al., Simulation of high-frequency sinusoidal electrical block of mammalian myelinated axons, J. Comput Neurosci (2007) 22:313-326.

* cited by examiner

SYSTEM AND METHOD FOR MODULATING ACTION POTENTIAL PROPAGATION DURING SPINAL CORD STIMULATION

RELATED APPLICATION

The present application claims the benefit under 35 U.S.C. §119 to U.S. provisional patent application Ser. No. 61/114,965, filed Nov. 14, 2008. The foregoing application is hereby incorporated by reference into the present application in its entirety.

FIELD OF THE INVENTION

The present invention relates to tissue stimulation systems, and more particularly, to a system and method for stimulating neural fibers.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic pain syndromes, and the application of spinal cord stimulation has begun to expand to additional applications, such as angina pectoralis and incontinence.

An implantable SCS system typically includes one or more electrode carrying stimulation leads, which are implanted at a stimulation site in proximity to the spinal cord tissue of the patient, and a neurostimulator implanted remotely from the stimulation site, but coupled either directly to the stimulation lead(s) or indirectly to the stimulation lead(s) via a lead extension. The neurostimulation system may further comprise a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer (CP), which typically includes a general purpose computer, such as a laptop, with a programming software package installed thereon.

Thus, programmed electrical pulses can be delivered from the neurostimulator to the stimulation lead(s) to stimulate or activate a volume of the spinal cord tissue. In particular, electrical stimulation energy conveyed to the electrodes creates an electrical field, which when strong enough, depolarizes (or "stimulates") the neural fibers within the spinal cord beyond a threshold level, thereby inducing the firing of action potentials (APs) that propagate along the neural fibers to provide the desired efficacious therapy to the patient.

The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include electrical pulse parameters, which may define the pulse amplitude, pulse width, pulse rate, pulse shape, and burst rate. Each electrode combination, along with the electrical pulse parameters, can be referred to as a "stimulation parameter set."

Stimulation energy may be delivered to the electrodes during and after the lead placement process in order to verify that the electrodes are stimulating the target neural elements and to formulate the most effective stimulation regimen (i.e., the best stimulation parameter set or sets). The stimulation regimen will typically be one that provides stimulation energy to all of the target tissue that must be stimulated in order to provide the therapeutic benefit, yet minimizes the volume of non-target tissue that is stimulated.

While the electrical stimulation of neural fibers has generally been successful in providing a therapeutic benefit to the patient, there are instances where the target tissue is not directly adjacent to an electrode and, because the electrical field strength decreases exponentially with distance from the electrodes, a relatively strong electrical field must be created to generate APs in the target neural fibers. The electrical field may, however, also result in the generation of APs in non-target neural fibers between the electrode and the target neural fibers. The generation of APs in the non-target neural fibers may, in turn, lead to undesirable outcomes (e.g., discomfort or involuntary movements) for the patient. Because the target neural tissue (i.e., the tissue associated with the therapeutic effects) and non-target neural tissue (i.e., the tissue associated with undesirable side effects) are often juxtaposed, therapeutically stimulating neural tissue while preventing side effects may be difficult to achieve. In the context of SCS, there may be a few ways of eliminating, or at least minimizing, the stimulation of non-target neural tissue.

For example, to provide pain relief without inducing involuntary motor movements or otherwise causing discomfort, the neural fibers in the dorsal column (DC neural fibers), which primarily include sensory neural fibers, may be preferentially stimulated over neural fibers in the dorsal roots (DR neural fibers), which include both innocuous sensory neural fibers and sensory fibers linked directly to motor reflexes.

It is believed that the antidromic activation (i.e., the APs propagate in a direction opposite to their normal direction, which in the case of the spinal cord DC neural fibers, propagate in the caudal direction) of the large diameter DC neural fibers provides the actual pain relief to the patient by reducing/blocking transmission of smaller diameter pain fibers via interneuronal interaction in the dorsal horn of the spinal cord, while the orthodromic activation (i.e., the APs propagate in their normal direction, which in the case of the spinal cord, propagate in the rostral direction) of the large diameter DC neural fibers generate APs that arrive at the thalamus and are relayed to the sensory cortex, thereby creating a typically innocuous side-effect in the form of a sensation known as paresthesia, which can be characterized as an tingling sensation.

Thus, it is believed that the large diameter DC neural fibers are the major targets for SCS for overlaying the patient's painful regions with paresthesia. It can then be appreciated that the clinical goal of pain relief can often be achieved by placing the electrodes of the stimulation lead(s) as near as possible to the innervating DC neural fibers associated with the dermatomic area of pain, and if necessary, "tuning" the electrical stimulation by adjusting one or more stimulation parameters. In some cases, this is relatively simple due to the relatively close proximity of the active stimulating electrodes to the innervating DC neural fibers, as well as the size and/or orientation of the stimulating electrodes relative to these DC neural fibers.

However, in many clinical situations, the targeted DC neural fibers are difficult to stimulate for the inverse of the above reasons. In these cases, stimulation tuning can be difficult and can require great skill, insight, and luck. Typically, such tuning entails confining the stimulating electrical field to a region of neural tissue that has a high likelihood of achieving concordant paresthesia using primarily electrode combination adjustments, and then attempting improve neural selectivity using electrical pulse parameter adjustments. This method, however, can be self-limiting. If the targeted neural fibers are close to, outnumbered by, and/or harder to stimulate than the non-targeted neural fibers, it may be that the non-targeted neural fibers are stimulated to a greater degree than the targeted neural fibers, or even to a degree that the patient finds intolerable. As a result, even if the DR neural fibers are not stimulated, over-stimulation of the DC neural fibers may occur, thereby resulting in a discomfort sensation that is thought to originate from the orthodromic propagation of the APs to the thalamus of the patient.

An example of this phenomenon is commonly experienced clinically. In particular, if the patient seeks concordant paresthesia for lower back pain, a stimulation lead may be placed along the spinal cord and the stimulation parameters selected to activate the DC neural fibers that innervate the L1-L2 dermatomes coincident with the lower back body region. However, the L1-L2 dermatomes are also coincident with the anterior legs. Because the DC neural fibers that innervate the lower back region are likely to be less prevalent and perhaps deeper in the spinal column than the DC neural fibers that innervate the anterior leg regions, it is likely that a great many anterior leg-innervating neural fibers will reside in the superficial layers of the dorsal column and will be activated at lower stimulation energy than the lower back-innervating neural fibers.

Thus, it is often the case that the patient will perceive leg paresthesia as the first paresthesia perception and, as the magnitude of the stimulation energy is increased in an attempt to achieve lower back paresthesia, the leg paresthesia grows more intense, while the lower back paresthesia is not yet achieved. At some point, the leg paresthesia becomes too intense to be tolerated, such that the magnitude of the stimulation energy may not be further increased. If the DC neural fibers that innervate the low back region are only partially stimulated, or not stimulated at all, at the maximum tolerated stimulation energy, then the therapy will be highly compromised (if existent).

There, thus, remains a need to minimize or eliminate any adverse effect that may otherwise result from the inadvertent stimulation of non-targeted neural tissue.

SUMMARY OF THE INVENTION

In accordance with a first aspect of the present invention, a method of providing therapy to a patient is provided. The method comprises conveying an electrical pulsed waveform between at least one caudal electrode and spinal cord tissue, thereby evoking action potentials that are orthodromically propagated along dorsal column (DC) neural fibers and evoking action potentials that are antidromically propagated along the DC neural fibers. In one method, the action potentials antidromically propagated along the DC neural fibers provide therapy to the patient, and the action potentials orthodromically propagated along the DC neural fibers create a sensation of paresthesia in the brain. If the therapy is pain relief, the DC neural fibers that are stimulated may innervate a region of pain experienced by the patient.

The method further comprises conveying electrical energy (e.g., a plurality of anodic electrical pulses that sinusoidally vary at a frequency greater than the pulse rate of the electrical pulsed waveform) between at least one rostral electrode and the spinal cord tissue, thereby modulating times that the action potentials orthodromically propagated along the DC neural fibers arrive at the brain of the patient. If the modulating electrical energy comprises a plurality of electrical pulses, the action potentials orthodromically propagated along the DC neural fibers and the modulating electrical pulses preferably overlap each other at a point of modulation in the DC neural fibers. In one method, the action potentials orthodromically propagated along the DC neural fibers would otherwise create an undesirable sensation in the absence of the electrical energy conveyed between the rostral electrode(s) and the spinal cord tissue.

In accordance with a second aspect of the present inventions, a method of providing therapy to a patient using first and second electrodes spaced along a first neural axon of the patient is provided. The method comprises conveying an electrical pulsed waveform through the first electrode, thereby evoking action potentials that are propagated along the first neural axon. In one method, the action potentials are orthodromically propagated along the first neural axon. For example, if the first neural axon is a dorsal column neural fiber, the action potentials may propagate along the neural fiber to the brain. In this case, the first electrode may be a caudal electrode, and the second electrode may be a rostral electrode.

The method further comprises conveying electrical energy (e.g., alternating electrical energy) through the second electrode, wherein the electrical energy has a frequency that is greater than a pulse rate of the electrical pulsed waveform, such that the action potentials propagated along the neural axon are modulated or blocked by the electrical energy. For example, the pulse rate of the electrical pulsed waveform may be within a range of 2 Hz-1200 Hz, and the frequency of the electrical energy may be greater than 1200 Hz, and preferably, equal to or greater than 2000 Hz.

In one method, the electrical pulse waveform conveyed through the first electrode evokes action potentials in a second neural axon that are not blocked by the electrical energy conveyed through the second electrode. The first neural axon may have a first depth in the spinal cord tissue, and the second neural axon may have a second greater depth in the neural tissue. For example, the first neural axon may be a dorsal column (DC) neural fiber that innervates a first body region (e.g., an anterior leg region) of the patient, and the second neural axon may be a DC neural fiber that innervates a second different body region (e.g., a lower back region) of the patient.

In accordance with a third aspect of the present inventions, a neurostimulator is provided. The neurostimulation comprises a plurality of electrical terminals configured for being electrically coupled to at least one electrode carrying stimulation lead, and analog output circuitry configured for conveying an electrical pulsed waveform to or from a first one of the electrical terminals, and for simultaneously conveying electrical energy (e.g., sinusoidally anodic electrical energy) to or from a second one of the electrical terminals in accordance with a set of stimulation parameters. The neurostimulator further comprises control circuitry configured for generating the set of stimulation parameters.

The electrical energy has a frequency that is greater than a pulse rate of the electrical pulsed waveform. For example, the pulse rate of the electrical pulsed waveform may be within a range of 2 Hz-1200 Hz, and the frequency of the electrical energy may be greater than 1200 Hz, and preferably, equal to or greater than 2000 Hz. In one embodiment, the electrical pulsed waveform is capable of evoking action potentials that are propagated along a first neural axon adjacent the stimulation lead, and the electrical energy is capable of modulating or blocking the action potentials propagated along the first neural axon. In one embodiment, the neurostimulator further comprises a case that contains the plurality of electrical terminals, analog output circuitry, and control circuitry to form an implantable neurostimulator.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
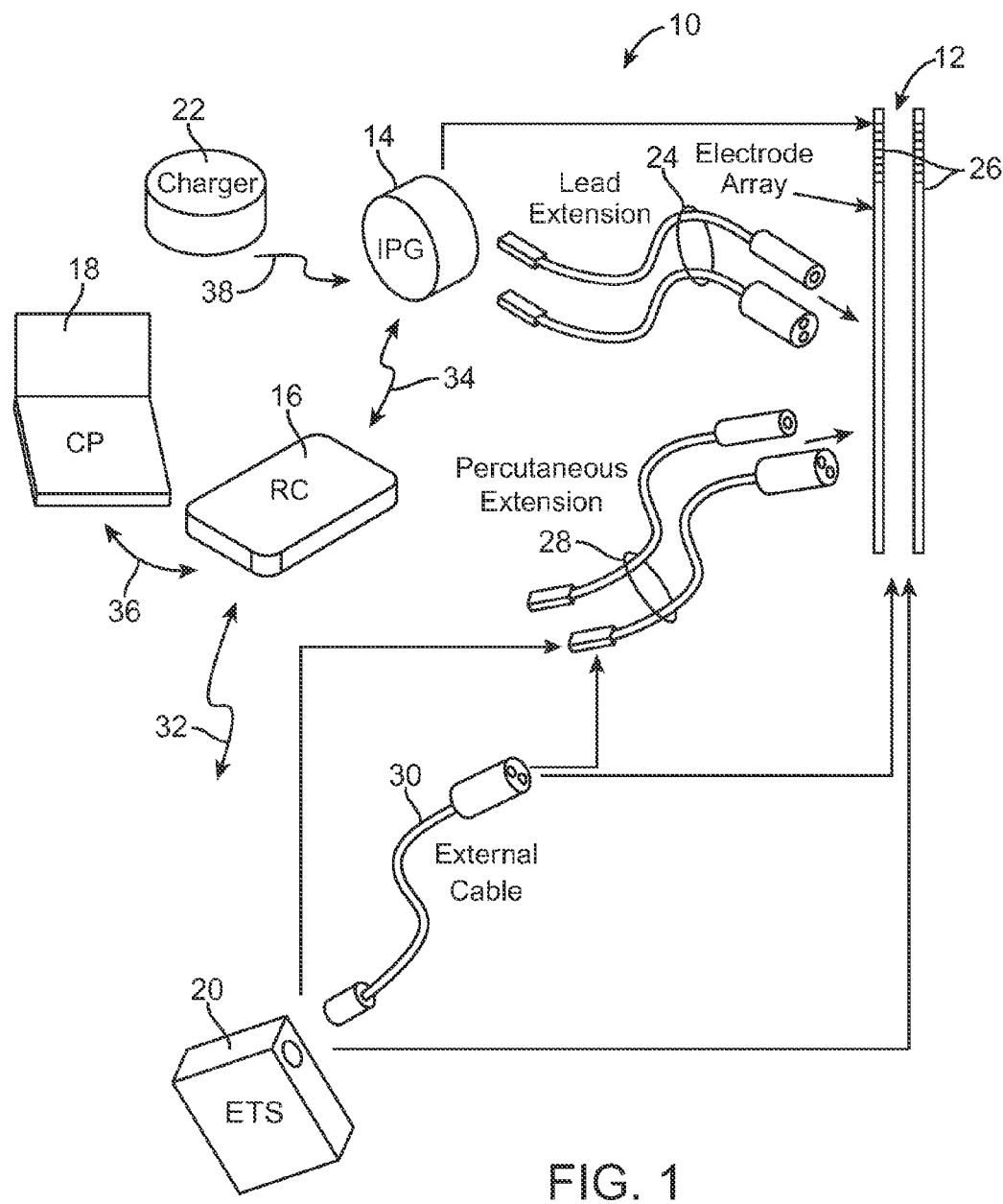
FIG. 1 is plan view of one embodiment of a spinal cord stimulation (SCS) system arranged in accordance with the present inventions.

Turning first to FIG. 1, an exemplary spinal cord stimulation (SCS) system 10 generally includes one or more (in this case, two) implantable stimulation leads 12, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
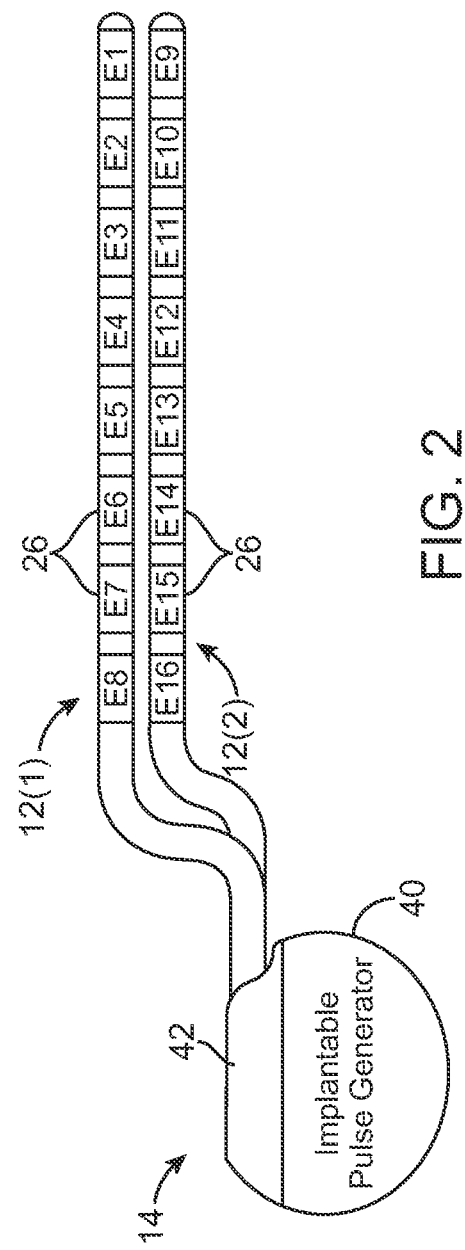
FIG. 2 is a plan view of an implantable pulse generator (IPG) and one embodiment of a stimulation lead used in the SCS system of FIG. 1.

Referring now to FIG. 2, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mate in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As briefly discussed above, the IPG 14 includes battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second), pulse shape, and burst rate (measured as the stimulation on duration per unit time).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and case 40. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

The IPG 14 also comprises circuitry configured for delivering electrical energy to the electrode array 26 in a manner that modulates and/or blocks action potentials (APs) that propagate along neural axons (which in the illustrated embodiment, are the dorsal column (DC) neural fibers) in response to the pulsed electrical stimulation energy. In one embodiment, the electrical energy takes the form of modulating electrical pulses that are capable of modulating the action potentials (APs) propagating along the DC neural fibers. In another embodiment, the electrical energy takes the form of a continuous high frequency signal capable of blocking the action potentials (APs) propagating along the DC neural fibers. Further details discussing the modulating/blocking electrical energy will be discussed below.

Figure 3:
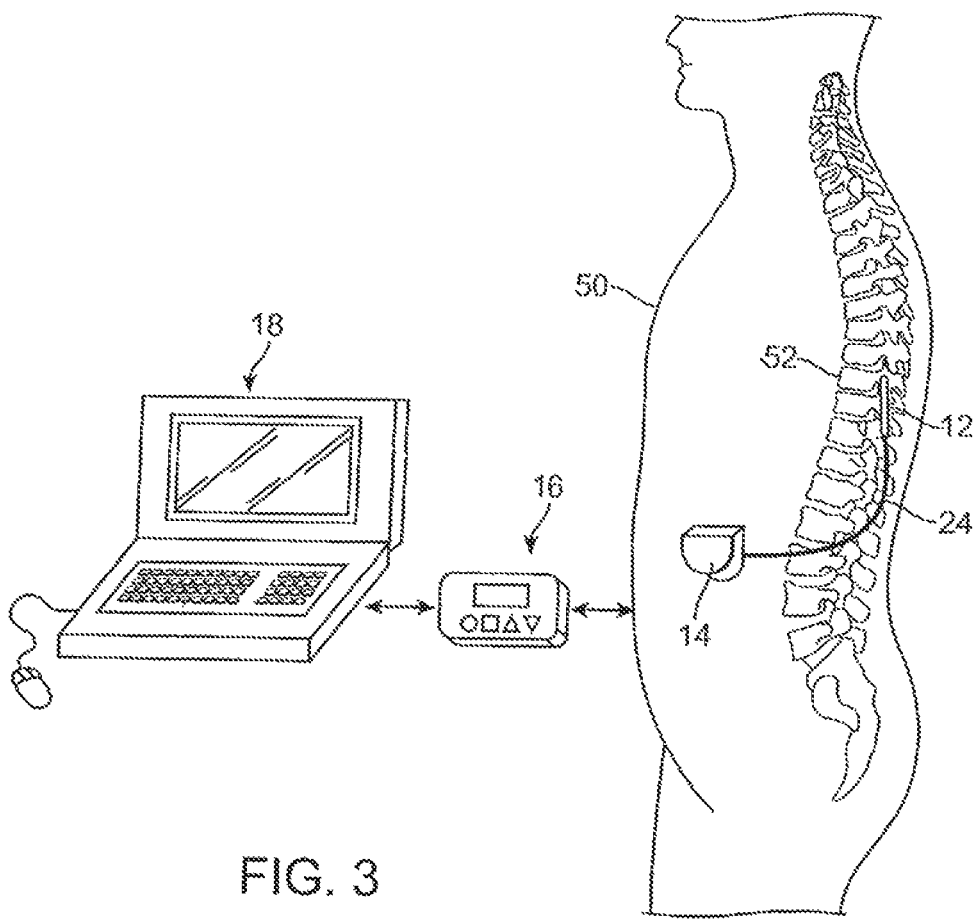
FIG. 3 is a plan view of the SCS system of FIG. 1 in use with a patient.

As shown in FIG. 3, the electrode leads 12 are implanted within the spinal column 52 of a patient 50. The preferred placement of the electrode leads 12 is adjacent, i.e., resting near, or upon the dura, adjacent to the spinal cord area to be stimulated. Due to the lack of space near the location where the electrode leads 12 exit the spinal column 52, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 4:
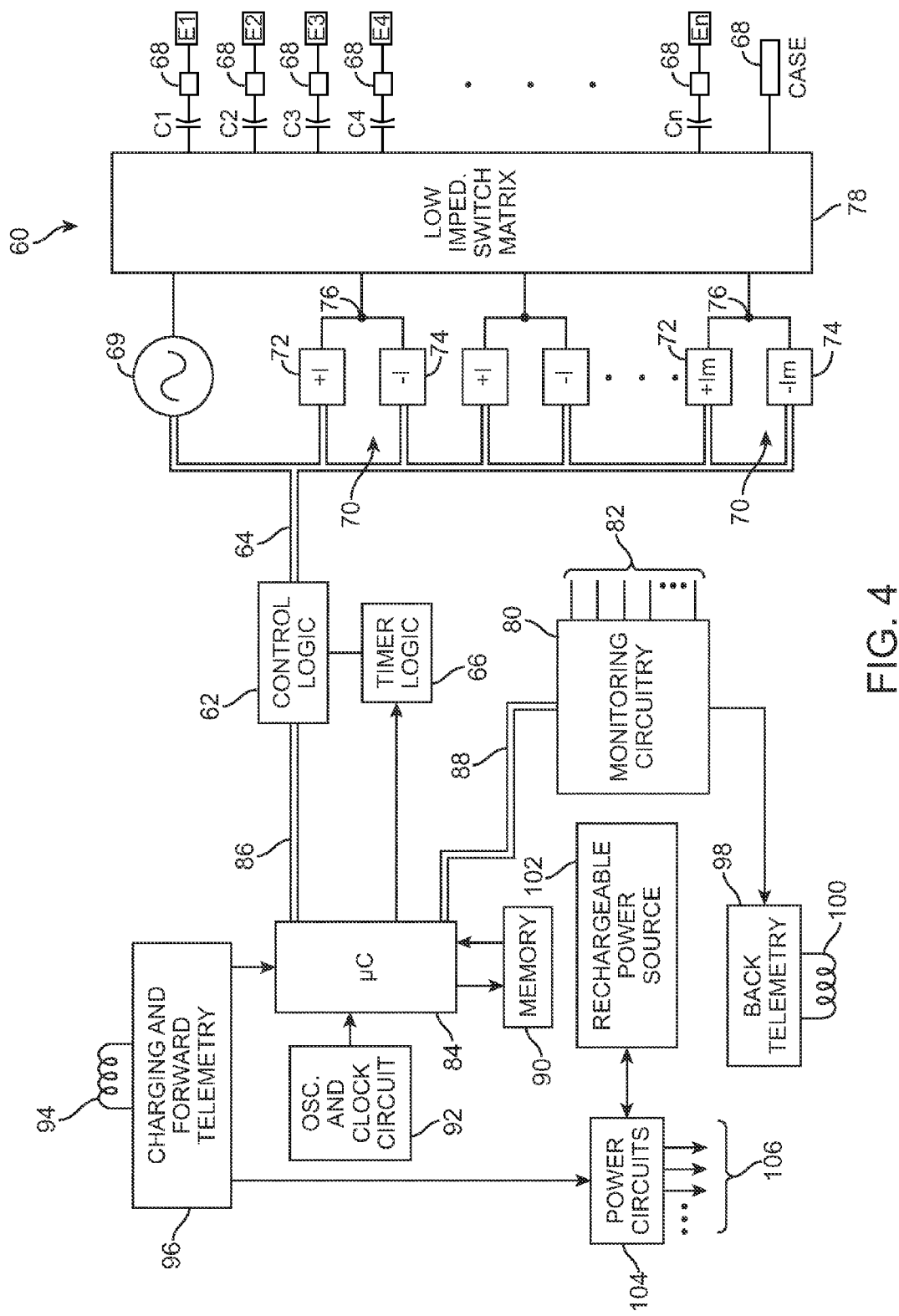
FIG. 4 is a block diagram of the internal components of the IPG of FIG. 2.

Turning next to FIG. 4, one exemplary embodiment of the IPG 14 will now be described. The IPG 14 includes analog output circuitry 60 configured for generating electrical stimulation energy in accordance with a defined pulsed waveform having a specified pulse amplitude, pulse rate, pulse duration, pulse shape, and burst rate under control of control logic circuitry 62 over data bus 64. The analog output circuitry 60 is further configured for generating AP modulating and/or blocking electrical energy, which in the illustrated embodiment, takes the form of an anodic (positively polarized) pulsed or continuous sinusoidal signal.

Control of the pulse rate and pulse duration of the electrical stimulation waveform, and if pulsed, the AP modulating and/or blocking electrical energy, is facilitated by timer logic circuitry 66, which may have a suitable resolution, e.g., 10 μs. In the illustrated embodiment, the pulse rate can be varied within the range of 2-1200 Hz. The stimulation energy generated by the analog output circuitry 60 is output via capacitors C1-C16 to electrical terminals 68 corresponding to electrodes E1-E16.

The analog output circuitry 60 comprises a plurality m independent current source pairs 70 capable of supplying the stimulation energy to the electrical terminals 68 at a specified and known amperage. One current source 72 of each pair 70 functions as a positive (+) or anodic current source, while the other current source 74 of each pair 70 functions as a negative (−) or cathodic current source. The outputs of the anodic current source 72 and the cathodic current source 74 of each pair 70 are connected to a common node 76.

The analog output circuitry 60 comprises a sinusoidal source 69 capable of supplying the AP modulating and/or blocking electrical energy in the form of a sinusoidal signal to the electrical terminals 68 at a specified and known amperage. The frequency of the signal generating by the sinusoidal source 69 is preferably greater than the pulse rate of the stimulation energy. In the illustrated embodiment, the frequency of the sinusoidal signal is greater than 1200 Hz, and preferably equal to or greater than 2000 Hz.

The analog output circuitry 60 further comprises a low impedance switching matrix 78 through which the common node 76 of each current source pair 70 is connected to any of the electrical terminals 68 via the capacitors C1-C16. Thus, for example, it is possible to program the first anodic current source 72 (+I1) to produce a pulse having a peak amplitude of +4 mA (at a specified rate and for a specified duration), and to synchronously program the second cathodic current source 74 (−I2) to similarly produce a pulse having a peak amplitude of −4 mA (at the same rate and pulse duration), and then connect the node 76 of the anodic current source 72 (+I1) to the electrical terminal 68 corresponding to electrode E3, and connect the node 76 of the cathodic current source 74 (−I2) to the electrical terminal 68 corresponding to electrode E1. The sinusoidal source 69 is also connected through the low impedance switching matrix 78 to any of the electrical terminals 68 via the capacitors C1-C16.

The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference. In an alternative embodiment, rather than using independent controlled current sources, independently controlled voltage sources for providing electrical pulses of a specified and known voltage at the electrical terminals 68 can be provided. The operation of this output circuitry, including alternative embodiments of suitable output circuitry for performing the same function of generating electrical pulses of a prescribed amplitude and width, is described more fully in U.S. Pat. Nos. 6,516,227 and 6,993,384, which are expressly incorporated herein by reference.

Hence, it is seen that each of the electrical terminals 68 can be programmed to have a modulation/blocking state (i.e., a sinusoidal current (pulsed or continuous) flows through the respective electrode), a stimulation state (i.e., a pulsed DC current (sourcing current or sinking current) flows through the respective electrode), or an off state (i.e., no current flows through the respective electrode). Further, the amplitude of the current for a given electrical terminal 68 may be programmed to one of several discrete levels.

In one embodiment, the current through each stimulating electrical terminal 68 can be individually set from 0 to ±10 mA in steps of 100 µA, within the output voltage/current requirements of the IPG 14. Additionally, in one embodiment, the total current output by a group of stimulating electrical terminals 68 can be up to ±20 mA (distributed among the electrodes included in the group). Moreover, it is seen that each of the stimulating electrical terminals 68 can operate in a multipolar mode, e.g., where two or more electrical terminals are grouped to source/sink current at the same time. Alternatively, each of the stimulating electrical terminals 68 can operate in a monopolar mode where, e.g., the electrical terminals 68 are configured as cathodes (negative), and case 40 of the IPG 14 is configured as an anode (positive). The peak-to-peak current of the sinusoidal signal conveyed through an AP modulating/blocking electrical terminal 68 can be individually set from 0 to ±10 mA in steps of 100 µA, within the output voltage/current requirements of the IPG 14. In the illustrated embodiment, the AP modulating/blocking electrical terminal 68 is operated in a monopolar mode where, e.g., the electrical terminal 68 is configured as an anode (positive) and the case of the IPG 14 is configured as a cathode (negative).

The analog output circuitry 60 may also comprise pulse shaping circuitry (not shown) capable of shaping the pulses (e.g., a square pulse, an exponential pulse, a logarithmic pulse, a ramped pulse, a trapezoidal pulse, etc.). Further details discussing pulse shaping circuitry and the different pulse shapes that can be generated are disclosed in U.S. Patent Application Ser. No. 60/951,177 (now abandoned), entitled "Use of Stimulation Pulse Shape to Control Neural Recruitment Order and Clinical Effect," which is expressly incorporated herein by reference.

An electrical terminal 68 (whether stimulating or AP modulating/blocking) may be included with any of up to k possible groups, where k is an integer corresponding to the number of timing channels, and in one embodiment, is equal to 4, and with each timing channel k having a defined pulse amplitude, pulse duration, and pulse rate. Other timing channels may be realized in a similar manner. Thus, each channel identifies which electrical terminals 68 (and thus electrodes) are stimulating or AP modulating/blocking, as well as the characteristics of the current (pulse amplitude, pulse duration, pulse rate, and pulse shape for pulsed current, and peak-to-peak amplitude for sinusoidal current) flowing through the electrical terminals 68 (and thus electrodes).

The IPG 14 further comprises monitoring circuitry 80 for monitoring the status of various nodes or other points 82 throughout the IPG 14, e.g., power supply voltages, temperature, battery voltage, and the like. The monitoring circuitry 80 is also configured for measuring electrical data at the electrodes 26 (e.g., electrode impedance and/or electrode field potential) necessary to determine whether each of the electrodes 26 is functioning properly and is properly coupled to the IPG 14.

The IPG 14 further comprises processing circuitry in the form of a microcontroller (µC) 84 that controls the control logic circuitry 62 over data bus 86, and obtains status data, and optionally physiological information, from the monitoring circuitry 80 via data bus 88. The µC 84 additionally controls the timer logic circuitry 66. The IPG 14 further comprises memory 90 and an oscillator and clock circuit 92 coupled to the microcontroller 84. Thus, the microcontroller 84, in combination with the memory 90 and oscillator and clock circuit 92, comprise a microprocessor system that carries out functions in accordance with a suitable program stored in the memory 90. Alternatively, for some applications, the functions provided by the microprocessor system may be carried out by a suitable state machine.

The microcontroller 84 generates the necessary control and status signals, which allow the microcontroller 84 to control the operation of the IPG 14 in accordance with the operating program and stimulation parameters stored in the memory 90. In controlling the operation of the IPG 14, the microcontroller 84 is able to individually generate stimulus pulses at the electrodes 26 using the analog output circuitry 60, in combination with the control logic circuitry 62 and timer logic circuitry 66, thereby allowing each electrode 26 to be paired or grouped with other electrodes 26, including the monopolar case electrode, and to control and modify the polarity, pulse amplitude, pulse rate, pulse duration, pulse shape, burst rate, and channel through which the current stimulus pulses are provided. The microcontroller 84 is also able to generate AP modulating/blocking electrical energy at selected ones of the electrodes 26 using the analog output circuitry 60, in combination with the control logical circuitry 62 and timer logic circuitry 66 (if needed), and to control and modify the pulse amplitude, pulse rate, pulse duration (if pulsed), and the channel through which the AP modulating/blocking electrical energy is provided.

The IPG 14 further comprises an alternating current (AC) receiving coil 94 for receiving programming data (e.g., the operating program and/or stimulation parameters) from the RC 16 in an appropriate modulated carrier signal, and charging and forward telemetry circuitry 96 for demodulating the carrier signal it receives through the AC receiving coil 94 to recover the programming data, which programming data is then stored within the memory 90, or within other memory elements (not shown) distributed throughout the IPG 14.

The IPG 14 further comprises back telemetry circuitry 98 and an alternating current (AC) transmission coil 100 for sending informational data sensed through the monitoring circuitry 80 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 102 and power circuits 104 for providing the operating power to the IPG 14. The rechargeable power source 102 may, e.g., comprise a lithium-ion or lithium-ion polymer battery. The rechargeable battery 102 provides an unregulated voltage to the power circuits 104. The power circuits 104, in turn, generate the various voltages 106, some of which are regulated and some of which are not, as needed by the various circuits located within the IPG 14. The rechargeable power source 102 is recharged using rectified AC power (or DC power converted from AC power through other means, e.g., efficient AC-to-DC converter circuits, also known as "inverter circuits") received by the AC receiving coil 104. To recharge the power source 102, an external charger (not shown), which generates the AC magnetic field, is placed against, or otherwise adjacent, to the patient's skin over the implanted IPG 14. The AC magnetic field emitted by the external charger induces AC currents in the AC receiving coil 104. The charging and forward telemetry circuitry 96 rectifies the AC current to produce DC current, which is used to charge the power source 102. While the AC receiving coil 104 is described as being used for both wirelessly receiving communications (e.g., programming and control data) and charging energy from the external device, it should be appreciated that the AC receiving coil 104 can be arranged as a dedicated charging coil, while another coil, such as coil 100, can be used for bi-directional telemetry.

It should be noted that the diagram of FIG. 4 is functional only, and is not intended to be limiting. Those of skill in the art, given the descriptions presented herein, should be able to readily fashion numerous types of IPG circuits, or equivalent circuits, that carry out the functions indicated and described. Additional details concerning the above-described and other IPGs may be found in U.S. Pat. No. 6,516,227, U.S. Patent Publication No. 2003/0139781, and U.S. patent application Ser. No. 11/138,632 (now U.S. Pat. No. 7,539,538), entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to the stimulation lead 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
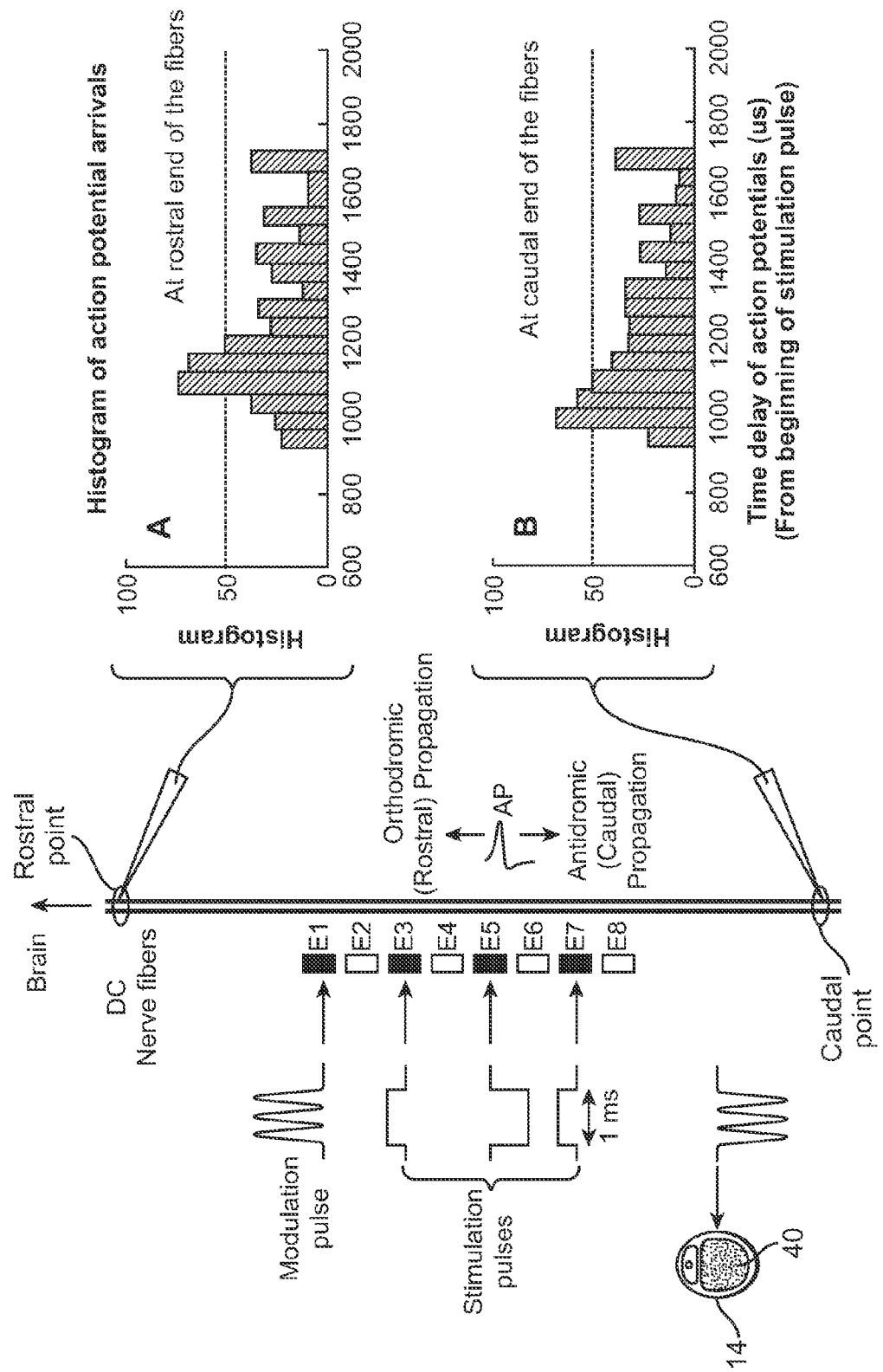
FIG. 5 is a plan view of electrodes stimulating dorsal column (DC) neural fibers to create action potentials (APs) and modulating the APs orthodromically propagating along the DC neural fibers, as well as histograms of AP arrivals at points rostral and caudal to the electrodes.

Referring now to FIG. 5, a method of using the SCS system 10 to modulate action potentials (APs) propagating along DC neural fibers to the brain will be described. As there shown, electrodes E1-E8 are rostro-caudally arranged along two DC neural fibers.

Electrodes E3, E5, and E7 are configured as stimulating electrodes in a tripolar arrangement, with electrodes E3 and E7 generating anodic pulses, and the intervening electrode E5 generating a cathodic pulse. The resulting stimulation evokes an action potential (AP) that both orthodromically propagates (in this case, in the rostral direction) and antidromically propagates (in this case, in the caudal direction) along each of the DC neural fibers.

As discussed above in the background of the invention, it is believed that the antidromic propagation of APs in DC neural fibers reduces/blocks transmission of smaller diameter pain fibers via interneuronal interaction in the dorsal horn of the spinal cord, while the orthodromic propagation of APs in DC neural fibers arrive at the thalamus and are relayed to the sensory cortex to create the paresthesia sensation. It should be noted that, although only two DC neural fibers are shown for purposes of brevity, in reality, APs will be evoked in many more DC neural fibers.

Electrode E1 is configured as a modulating electrode in a monopolar arrangement with the case 40 of the IPG 14. Electrode E1, which is rostrally located relative to the stimulating electrodes E3, E5, and E7, generates a sinusoidal anodic pulse that modulates the APs rostrally propagating along the DC neural fibers. The APs caudally propagating along the DC neural fibers are not modulated. Although the modulating pulse is illustrated and described as being a sinusoidal pulse, the modulation pulse may be any anodic waveform (e.g., square, exponentially increasing/decreasing, trapezoidal, triangular, ramp, etc.). The optional pulse shaping circuitry described above with respect to the IPG 14 can be used to shape the pulses.

In the illustrated embodiment, the generation of the modulation pulse is timed, such that the modulation pulse overlaps the APs at the points of modulation along the DC neural fibers. Thus, the modulation pulse will be generated a certain time after the generation of the stimulation pulse, which time or delay will depend on an assumed propagation time of the APs from the points of stimulation on the DC neural fibers (adjacent to the anodic stimulation electrode, and in the illustrated case 40, electrode E5) to the points of modulation on the DC neural fibers (adjacent to the modulating electrode, and in this case, electrode E1). In alternative embodiments, the modulation pulse, instead of being concurrent with the APs (i.e., overlapping the APs), may be generated as a pre-pulse or a post-pulse that arrives at the points of modulation just prior or just subsequent to the APs.

Figure 6:
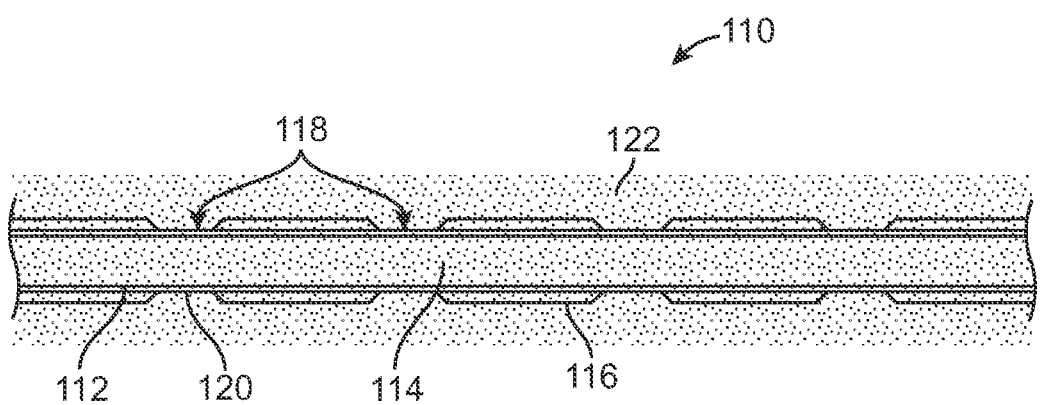
FIG. 6 is a cross-sectional view of a typical neuron.

To better understand the effect of conditioning and modulating pulses on nerve tissue, reference to FIG. 6 will now be made. As there shown, a typical neuron 110 that can be found in the white matter of the spinal cord or brain includes an axon 112 containing ionic fluid (and primarily potassium and sodium ions) 114, a myelin sheath 116, which is formed of a fatty tissue layer, coating the axon 112, and a series of regularly spaced gaps 118 (referred to as "Nodes of Ranvier"), which are typically about 1 micrometer in length and expose a membrane 120 of the axon 112 to extracellular ionic fluid 122.

When an action potential (i.e., a sharp electrochemical response) is induced within the neuron 110, the transmembrane voltage potential (i.e., a voltage potential that exists across the membrane 120 of the axon 112) changes, thereby conducting a neural impulse along the axon neuron 110 as sodium and potassium ions flow in and out of the axon 112 via ion channels in the membrane 120. Because ion flow can only occur at the nodes 118 where the membrane 120 of the axon 112 is exposed to the extracellular ionic fluid 122, the neural impulse will actually jump along the axon 112 from one node 116 to the next node 116. In this manner, the myelin sheath 116 serves to speed the neural impulse by insulating the electrical current and making it possible for the impulse to jump from node 116 to node 116 along the axon 112, which is faster and more energetically favorable than continuous conduction along the axon 112.

Further details discussing the electro-chemical mechanisms involved with propagating an AP along a neuron are disclosed in U.S. patent Ser. No. 11/752,895 (now U.S. Pat. No. 7,742,810), entitled "Short Duration Pre-Pulsing to Reduce Stimulation-Evoked Side-Effects," which is expressly incorporated herein by reference.

Ultimately, the propagation speed of an AP within a DC neural fiber will depend on the diameter of the neural fiber and precondition (transmembrane voltage potential and ion-channel status) of each node of Ranvier where an AP will be fired. Thus, in response to a single stimulation pulses, the APs evoked in multiple DC neural fibers will arrive at the thalamus at different times, but will be synchronized in a manner that creates the paresthesia sensation. The modulation of the APs via the modulating sinusoidal anodic pulse, however, will hyperpolarize the membrane voltage potentials of the DC neural fibers, thereby changing the speeds at which the APs propagate along the respective DC neural fibers. As a result, the AP arrival times at the thalamus are altered, thereby desynchronizing the APs.

Referring back to FIG. 5, a conventional neural fiber modeling technique was used to model the arrival times of APs at a point rostral to the modifying electrode and at a point caudal to the stimulating electrodes for a number of DC neural fibers. A fiber diameter of 14 μm, a spinal cord fluid depth (dCSF) of 2.0 mm, and a stimulation current of 1.4 times the dorsal root fiber stimulation threshold (1.4DRth) were assumed. The model also assumes that the rostral and caudal AP arrival points are equi-distance from the cathodic stimulation electrode, and therefore, without modulation, the distribution of AP arrival times at the rostral and caudal points should be the same. However, as shown by the AP arrival histograms in FIG. 5, the arrival times at the rostral point has been redistributed by the sinusoidal anodic modulation pulse, and therefore, the arrival times of the AP at the thalamus will be redistributed (i.e., desynchronized).

Figure 7:
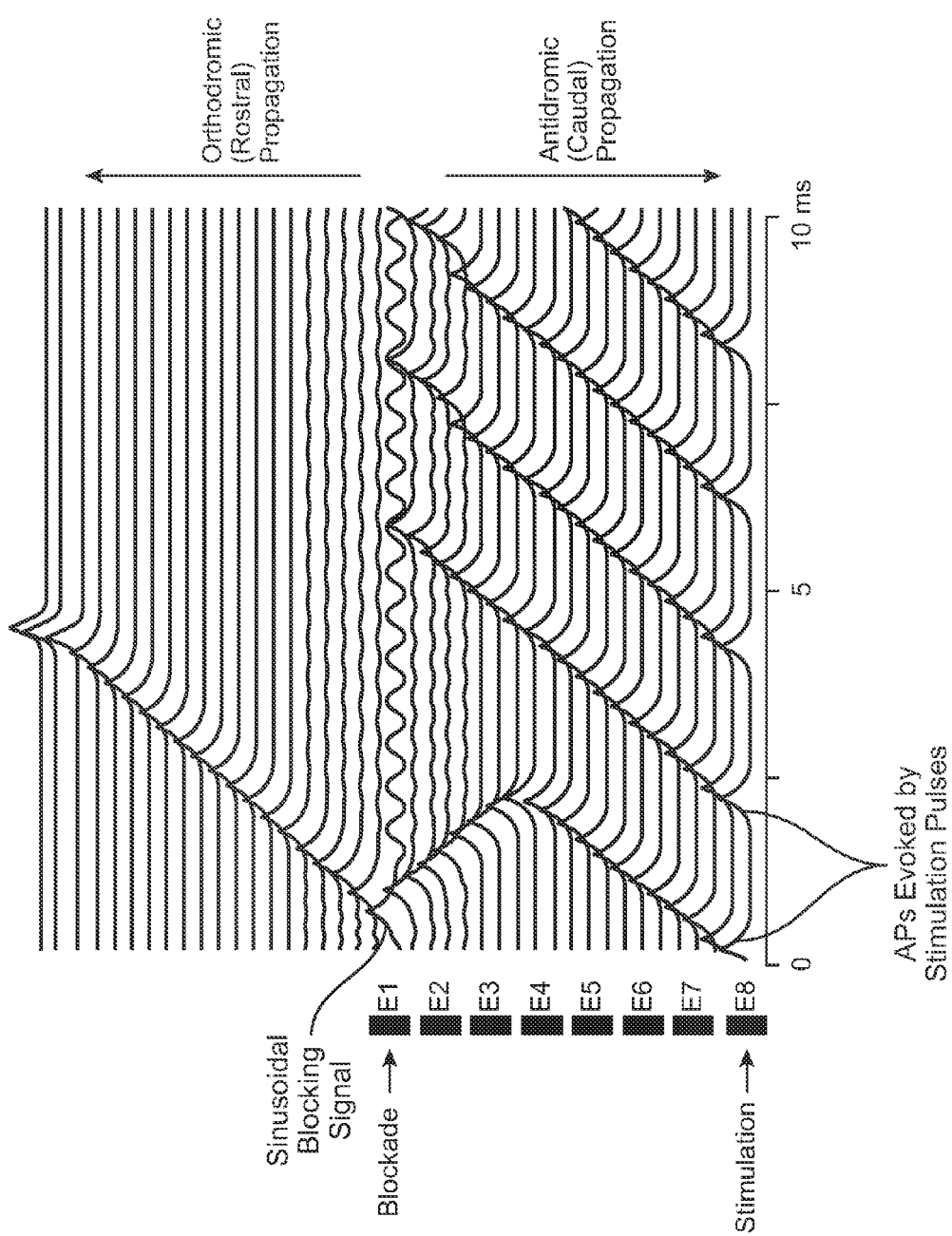
FIG. 7 is a plot illustrating APs propagating in the rostro-caudal space and a high frequency sinusoidal signal for blocking the AP orthodromically propagating along the DC neural fibers.

Referring now to FIG. 7, a method of using the SCS system 10 to block action potentials (APs) propagating along DC neural fibers to the brain will be described. As there shown, electrodes E1-E8 are rostro-caudally arranged along the spinal cord. A corresponding action potential (AP) plot generated using a conventional neural fiber modeling technique is also shown, wherein the horizontal axis represents time, and the vertical axis represents the rostrocaudal space.

Electrode E8 is configured as a stimulating electrode in a monopolar arrangement with the case of the IPG 14, and generates an anodic pulse, with the resulting stimulation evoking an action potential (AP) that orthodromically propagates (in this case, in the rostral direction) along the DC neural fibers. Electrode E1 is configured as a blocking electrode in a monopolar arrangement with the case 40 of the IPG 14 (not shown in FIG. 7). Electrode E1, which is rostrally located relative to the stimulating electrode E8, simultaneously with the generation of the stimulation pulses, generates a continuous sinusoidal blocking signal that has a high frequency relative to the pulse rate of the stimulation pulse waveform.

As there shown, one AP is evoked at the beginning of the sinusoidal blocking signal that orthodromically and antidromically propagates along the DC neural fibers. However, no further APs are evoked by the sinusoidal blocking signal. When the APs evoked by each stimulation pulse generated by the stimulation electrode E8 arrive at the region of blockade adjacent the blocking electrode E1, they are blocked are do not further propagate in the rostral direction, and therefore, never arrive at the thalamus of the brain.

Figure 8A:
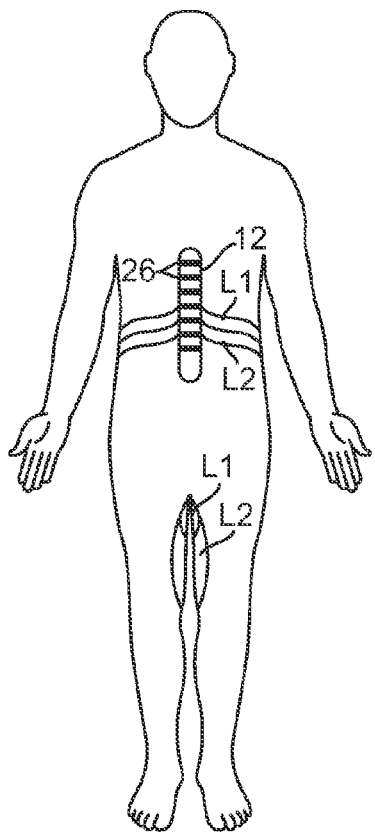
FIG. 8a is a posterior view of a patient, particularly showing the L1-L2 dermatomes.
Figure 8B:
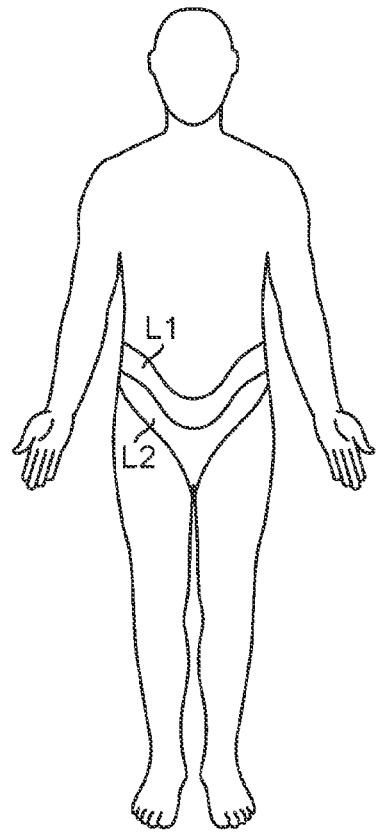
FIG. 8b is an anterior view of a patient, particularly showing the L1-L2 dermatomes.
Figure 9:
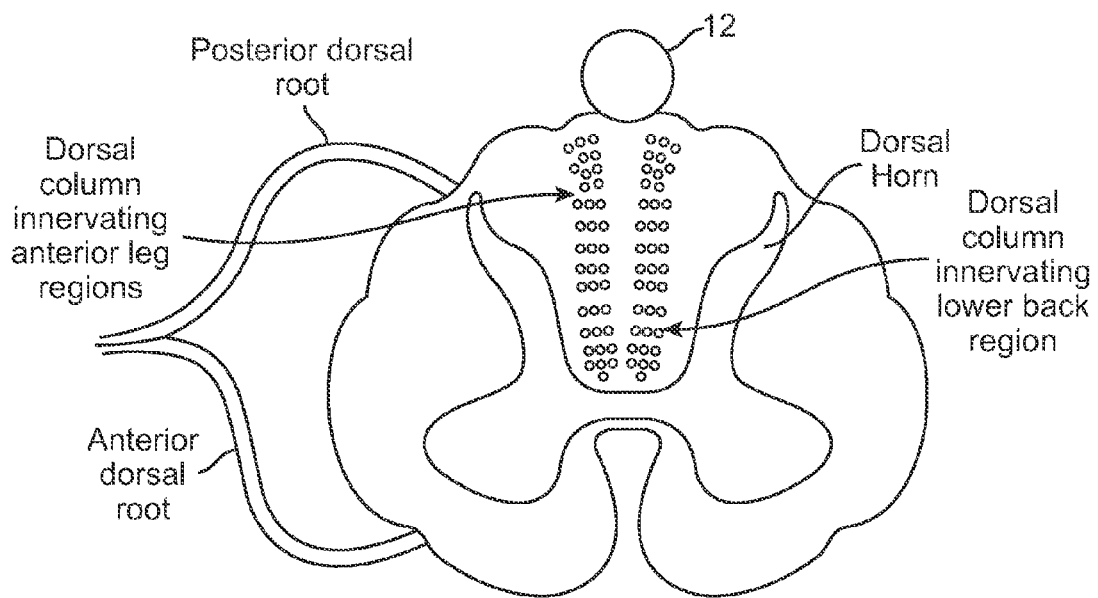
FIG. 9 is a cross-sectional view of a spinal cord.

Referring to FIGS. 8a, 8b, and 9, one method of using the SCS system 10 to provide pain therapy to a patient will be described. In this case, it is assumed that the patient suffers from chronic pain in the lower back. As there shown, the surgeon/clinician implants one or both stimulation leads 12 (only one shown for clarity) along the portion of the spinal cord adjacent the dorsal root (DR) neural fibers that innervate the targeted region, and in this case, the L1-L2 dermatomes containing the lower back region. As shown, a substantial length of the stimulation leads 12 lies over the L1-L2 dermatomes, with the distal end of the stimulation lead 12 being placed rostral of the L1-L2 dermatomes. The surgeon/clinician programs the IPG 14 with the CP 18 (shown in FIG. 1) to select the stimulation parameter set that recruits the dorsal column (DC) neural fibers that interact, via the dorsal horn, with the posterior DR neural fibers that innervate the L1-L2 dermatomes.

As discussed above in the background of the invention, the L1-L2 dermatomes also contain the anterior leg regions of the patient via the anterior DR neural fibers, and that the DC neural fibers that innervate the anterior leg regions of the patient will typically be recruited before the DC neural fibers that innervate the lower back region of the patient, thereby creating the paresthesia sensation within the anterior leg regions before the lower back region. Thus, as the amplitude of the stimulation pulses are increased in order to recruit the lower back innervating DC neural fibers (with the accompanying paresthesia sensation in the lower back region), the paresthesia sensation within the anterior leg regions may, without modulation of the APs orthodromically propagating in the DC neural fibers, become too uncomfortable.

Having priori knowledge of the phenomenon, the surgeon/clinician operates the IPG 14 via the CP 18 to convey electrical stimulation pulses between the electrodes of the stimulation lead(s) and the spinal cord tissue in accordance with the selected stimulation parameter set, and gradually increases the amplitude of the stimulation pulses, thereby increasingly recruiting DC neural fibers (i.e., evoked action potentials (APs) both orthodromically propagate and antidromically propagate along the DC neural fibers).

If the maximum tolerable stimulation energy accompanies by intense sensation in the non-target regions (in this case, the anterior leg regions) is reached without the patient reporting paresthesia concordant with the targeted region (i.e., the lower back region), the surgeon/clinician (under the assumption that the orthodromic propagation of APs along the DC neural fibers to the brain is the driving force for the patient's experience of intense sensations) will operate the IPG 14 via the CP 18 to convey, simultaneously with the conveyance of the stimulation pulses, modulation/blocking signals between one or more selected electrodes 26 rostrally located relative to the caudal combination of stimulating electrodes 26 and the spinal cord tissue, such that the APs orthodromically propagated along the DC neural fibers that innervate the anterior leg regions are modulated/blocked, thereby modifying the timing (i.e., desynchronizing) of the APs or blocking the AP from arriving at the thalamus of the patient.

Preferably, the modulation/blocking signals are delivered to the spinal cord tissue at an amplitude that primarily or only affects the propagation of APs in the superficial layers of the dorsal column where the anterior-leg innervating DC neural fibers are more prevalent, such that the orthodromic propagation of APs in the deeper lower back-innervating DC neural fibers are minimally or not affect at all, thereby allowing the patient to continue to perceive comfortable paresthesia in the lower back region.

The surgeon/clinician then operates the IPG 14 via the CP 18 to increase the amplitude of the modulating/blocking signals until the patient reports a reduction in the intense sensations, after which the amplitude of the stimulation pulses is further gradually increased, thereby recruiting more DC neural fibers with the goal of recruiting those that innervate the lower back region of the patient. If the patient again reports a perceived intense sensation in the anterior leg regions, the surgeon/clinician can again operate the IPG 14 via the CP 18 to increase the amplitude of the modulating/blocking signals until the patient again reports a reduction in the intense sensations.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulator, comprising:
    a plurality of electrical terminals configured for being electrically coupled to at least one electrode carrying stimulation lead;
    analog output circuitry configured for conveying an electrical pulsed waveform to or from a first one of the electrical terminals simultaneous with conveying sinusoidal electrical energy to or from a second one of the electrical terminals in accordance with a set of stimulation parameters, wherein the electrical energy has a frequency that is greater than a pulse rate of the electrical pulsed waveform; and
    control circuitry configured for generating the set of stimulation parameters.

2. The neurostimulator of claim 1, wherein the electrical pulsed waveform is capable of evoking action potentials that are propagated along a neural axon adjacent the stimulation lead, and the electrical energy is capable of blocking the action potentials propagated along the neural axon.

3. The neurostimulator of claim 1, wherein the pulse rate of the electrical pulsed waveform is within a range of 2 Hz-1200 Hz, and the frequency of the electrical energy is greater than 1200 Hz.

4. The neurostimulator of claim 3, wherein the frequency of the electrical energy is equal to or greater than 2000 Hz.

5. The neurostimulator of claim 1, further comprising a case containing the plurality of electrical terminals, analog output circuitry, and control circuitry to form an implantable neurostimulator.

6. The neurostimulator of claim 1, wherein the sinusoidal electrical energy is an electrical sinusoidally varying pulse.

7. A method of providing therapy to a patient using the neurostimulator of claim 1, comprising:
    conveying the electrical pulsed waveform via the first electrical terminal between at least one caudal electrode and spinal cord tissue, thereby evoking action potentials that are orthodromically propagated along dorsal column (DC) neural fibers and evoking action potentials that are antidromically propagated along the DC neural fibers; and
    conveying the electrical energy via the second electrical terminal between at least one rostral electrode and the spinal cord tissue, thereby modulating times that the action potentials orthodromically propagated along the DC neural fibers arrive at the brain of the patient.

8. The method of claim 7, wherein the action potentials antidromically propagated along the DC neural fibers provide therapy to the patient.

9. The method of claim 8, wherein the action potentials orthodromically propagated along the DC neural fibers create a sensation of paresthesia in the brain.

10. The method of claim 8, wherein the therapy is pain relief.

11. The method of claim 10, wherein the DC neural fibers innervate a region of pain experienced by the patient.

12. The method of claim 7, wherein the electrical energy conveyed between the at least one rostral electrode and the spinal cord tissue comprises a plurality of modulating electrical pulses.

13. The method of claim 12, wherein the modulating electrical pulses are anodic electrical pulses.

14. The method of claim 12, wherein each of the modulating electrical pulses sinusoidally varies.

15. The method of claim 14, wherein each of the modulating electrical pulses sinusoidally varies at a frequency greater than a pulse rate of the electrical pulsed waveform.

16. The method of claim 12, wherein the action potentials orthodromically propagated along the DC neural fibers and the modulating electrical pulses overlap each other at a point of modulation in the DC neural fibers.

17. The method of claim 7, wherein the action potentials orthodromically propagated along the DC neural fibers would otherwise create an undesirable sensation in the absence of the electrical energy conveyed between the at least one rostral electrode and the spinal cord tissue.

18. A method of providing therapy to a patient using the neurostimulator of claim 1 and first and second electrodes spaced along a first neural axon of the patient, comprising:
    conveying an electrical pulsed waveform via the first terminal through the first electrode, thereby evoking action potentials that are propagated along the first neural axon; and
    conveying electrical energy via the second terminal through the second electrode, wherein the electrical energy has a frequency that is greater than a pulse rate of the electrical pulsed waveform, such that the action potentials propagated along the first neural axon are blocked by the electrical energy.

19. The method of claim 18, wherein the action potentials are orthodromically propagated along the first neural axon.

20. The method of claim 19, wherein the first neural axon is a dorsal column (DC) neural fiber.

21. The method of claim 20, wherein the first electrode is a caudal electrode, and the second electrode is a rostral electrode.

22. The method of claim 18, wherein the electrical pulse waveform conveyed through the first electrode evokes action potentials in a second neural axon that are not blocked by the electrical energy conveyed through the second electrode.

23. The method of claim 22, wherein the first neural axon has a first depth in the spinal cord tissue, and the second neural axon has a second greater depth in the neural tissue.

24. The method of claim 23, wherein the first neural axon is a dorsal column (DC) neural fiber that innervates a first body region of the patient, and the second neural axon is a DC neural fiber that innervates a second different body region of the patient.

25. The method of claim 24, wherein the first body region is an anterior leg region of the patient, and the second body region is the lower back region of the patient.

26. The method of claim 18, wherein the electrical energy is anodic.

27. The method of claim 18, wherein the electrical energy is sinusoidal.

28. The method of claim 18, wherein the pulse rate of the electrical pulsed waveform is within a range of 2 Hz-1200 Hz, and the frequency of the electrical energy is greater than 1200 Hz.

29. The method of claim 18, wherein the frequency of the electrical energy is equal to or greater than 2000 Hz.

* * * * *